United States Patent [19]

Eppley et al.

[11] Patent Number: 5,658,516
[45] Date of Patent: Aug. 19, 1997

[54] METHOD OF MAKING A PROSPTHETIC IMPLANT

[75] Inventors: Barry Eppley, Indianapolis, Ind.; Thomas Sander, Newtown; Robert D. Torgerson, Branford, both of Conn.

[73] Assignee: United States Surgical Corporation, Norwalk, Conn.

[21] Appl. No.: 444,033

[22] Filed: May 18, 1995

Related U.S. Application Data

[62] Division of Ser. No. 69,452, Jun. 1, 1993, Pat. No. 5,496,371, which is a continuation of Ser. No. 712,987, Jun. 10, 1991, abandoned.

[51] Int. Cl.$^6$ .......................... B29C 45/14; B29C 33/12
[52] U.S. Cl. .......................... 264/251; 264/255; 264/275
[58] Field of Search .......................... 264/250, 251, 264/252, 255, 259, 254, 275

[56] References Cited

U.S. PATENT DOCUMENTS

| Re. 32,972 | 7/1989 | Harvey, Sr. et al. | |
|---|---|---|---|
| D. 270,373 | 8/1983 | Straith. | |
| D. 290,877 | 7/1987 | Giampapa et al. | |
| D. 290,878 | 7/1987 | Giampapa et al. | |
| D. 290,879 | 7/1987 | Giampapa et al. | |
| 374,572 | 12/1887 | Beale, Jr. | |
| 1,688,621 | 10/1928 | Huber. | |
| 2,672,686 | 3/1954 | Herzberg. | |
| 2,826,814 | 3/1958 | Sappey et al. | |
| 3,809,733 | 5/1974 | Sandiford et al. | 425/812 |
| 3,882,858 | 5/1975 | Klemm. | |
| 3,987,789 | 10/1976 | Timm et al. | |
| 4,186,448 | 2/1980 | Brekke. | |
| 4,267,608 | 5/1981 | Bora, Jr. | |
| 4,313,232 | 2/1982 | Habal et al. | |
| 4,360,342 | 11/1982 | Salvo. | |
| 4,362,509 | 12/1982 | Sulc. | |
| 4,392,562 | 7/1983 | Burton et al. | |
| 4,393,728 | 7/1983 | Larson et al. | |
| 4,448,741 | 5/1984 | Schad | 264/251 |
| 4,636,215 | 1/1987 | Schwartz. | |
| 4,636,347 | 1/1987 | Kato | 264/251 |
| 4,693,721 | 9/1987 | Ducheyne. | |
| 4,790,849 | 12/1988 | Terino. | |
| 4,888,018 | 12/1989 | Giampapa. | |
| 4,917,701 | 4/1990 | Morgan. | |
| 4,921,671 | 5/1990 | Staheli | 264/251 |
| 4,955,910 | 9/1990 | Bolesky. | |
| 4,969,901 | 11/1990 | Binder. | |
| 4,990,160 | 2/1991 | Terino. | |
| 4,997,446 | 3/1991 | Thoma. | |
| 5,087,259 | 2/1992 | Krenkel. | |
| 5,156,777 | 10/1992 | Kaye | 264/227 |
| 5,336,460 | 8/1994 | Hettinga | 264/251 |

FOREIGN PATENT DOCUMENTS

| 0398497 | 4/1990 | European Pat. Off. |
| 1960087 | 1/1969 | Germany. |
| 7412032 | of 0000 | Netherlands. |
| 8606954 | 5/1985 | WIPO. |
| 8903663 | 10/1988 | WIPO. |

Primary Examiner—Angela Ortiz

[57] ABSTRACT

Flexible prosthetic implants for repairing, replacing or augmenting hard tissue or bone. The flexible implant comprises a plurality of segments that are connected by flexible retainers which enable the segments to be re-oriented in relation to one another to accommodate the contour, size and shape of the body part being treated. A method for making such flexible prosthetic implants is also disclosed.

4 Claims, 10 Drawing Sheets

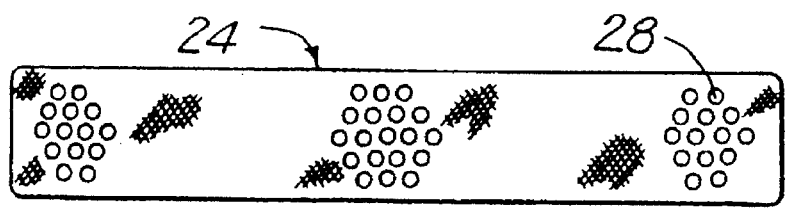
FIG.9
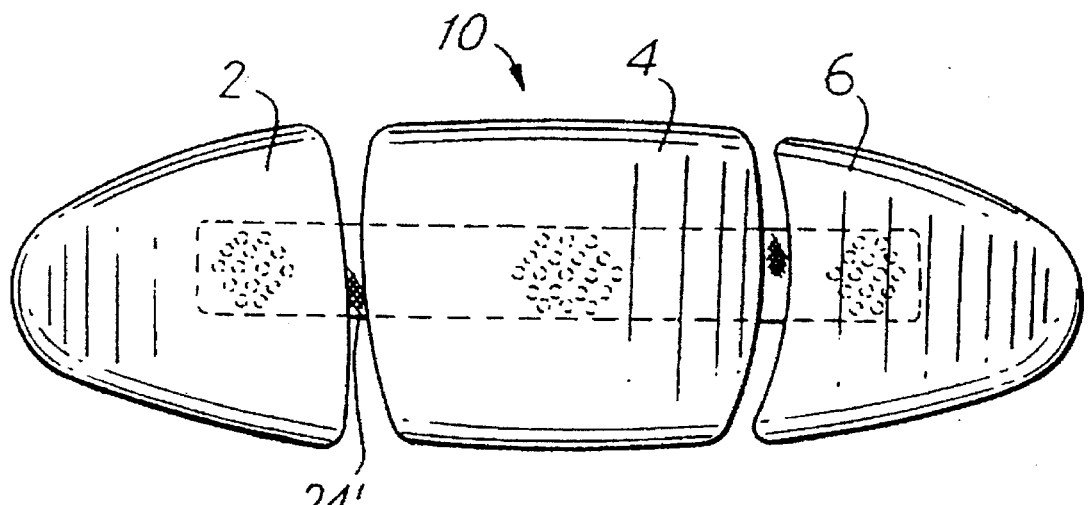
FIG.10
FIG.11
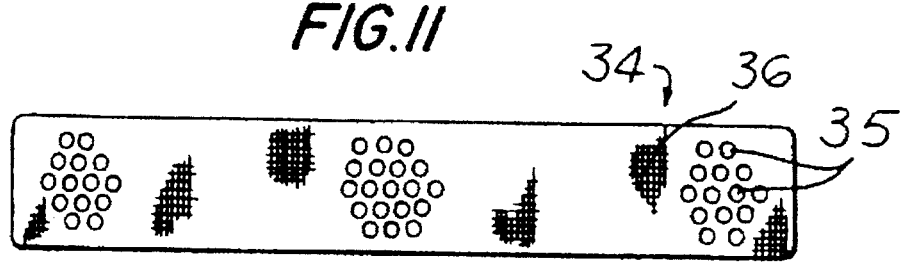

METHOD OF MAKING A PROSPTHETIC IMPLANT

This is a divisional of U.S. application Ser. No. 08/69,452 filed Jun. 1, 1993, now U.S. Pat. No. 5,496,371, which is a continuation of U.S. application Ser. No. 07/712,987 filed on Jun. 10, 1991, which is now abandoned.

BACKGROUND OF THE INVENTION

1. Field of the Invention

This invention relates to prosthetic implants and more particularly to flexible prosthetic implants for repair or replacement of hard tissue or bone which can be readily shaped to accommodate the body structure of the particular patient.

2. Description of the Related Art

Prosthetic implants are commonly used by physicians and other health care practitioners to replace, repair or augment hard tissue or bone in the body of a patient. These implants are utilized when a body part is mutilated or damaged through trauma or disease and as replacements or augmenters in cosmetic or plastic surgery.

Various materials are known in the art which can be used for making. prosthetic implants. Examples of such materials are chromium-cobalt-molybdenum alloys, stainless steel, titanium alloys, ceramics and various polymers and polymer/ceramic composites. Any materials used for prosthetics must be biologically compatible, i.e., they must not adversely affect living tissue and the environment created by living tissue must not adversely affect the prosthetic.

In many cases, prosthetic implants must replace or augment body parts such as bone which are rigid. Consequently, the implants need to be composed of a rigid material. Additionally, the implants need to approximate the size and shape of the body part being replaced or augmented. Because every patient is unique, a problem which often confronts practitioners is fashioning the implant to the requisite shape and proper fit, especially in the instances where rigid implants are required.

In some prior art methods, an implant is formed by making a mold of the body part of the individual patient and then deriving a custom prosthetic implant from the mold. The problem associated with this method is that it is time consuming due to the additional step required of making the mold. This also translated into higher costs for the patient. In other prior art methods, a prosthetic implant is formed to the approximate size and shape of the body part and is subsequently carved or sculpted to the exact dimensions of the particular patient. The problem associated with achieving the precise size and shape is compounded when the prosthetic implant is composed of rigid material because once the implant is formed it is time consuming and difficult to make adjustments to its size and shape. Any mistakes made in adjusting the configuration are difficult to correct and may require the fabrication of an entirely new implant.

Standardized preformed rigid implants have also been utilized. However, these standardized implants cannot account for differences in the bone or tissue structure among patients and therefore they also have to be individually carved to the necessary shape.

Additionally, in some surgical situations, the implants may be required to be inserted to the implant site via a tortuous or curved pathway. Rigid implants may fracture when being inserted along such pathway.

Therefore, the need exists for a prosthetic implant, formed of a rigid material, which can accommodate the needs of individual patients without requiring each implant to be separately molded or individually sculpted to the required configuration. Such implants would avoid the time consuming and expensive surgical procedures of the prior art.

SUMMARY OF THE INVENTION

The prosthetic implant of the present invention provides an adaptable standardized implant that can accommodate the needs of the particular patient while avoiding the time consuming individualized molding or sculpting required in the aforementioned prior art procedures. This is achieved by providing an implant comprised of a plurality of spaced apart segments attached by flexible connecting members which can be bent to re-orient the segments so that the implant approximates the size and shape of the body part being treated. The flexible connecting members may be sufficiently rigid so that when they are bent they maintain the contour of the bend after the bending force is no longer applied. Alternately, the flexible connecting members may be resilient such that after they are bent, they will return to their original shape.

The flexibility of the implant allows a practitioner to quickly customize it so it can conform to the contour of the patient's body and not detrimentally affect the patient's cosmetic appearance. Additionally, the flexibility advantageously allows the implants to be introduced into the implant site via a curved or tortuous pathway without fracturing. The implants of the present invention are well-suited for applications involving replacement, repair or augmentation of maxillofacial components.

The present invention also includes a method for making flexible prosthetic implants which involves partially filling a mold having two spaced apart cavities, placing a flexible retainer (connecting member) between the two partially filled cavities so the retainer extends partially into each cavity, filling the mold to cover the retainer, curing the material and removing the material from the mold.

BRIEF DESCRIPTION OF THE DRAWINGS

FIG. 9 is a front plan view of still another alternate embodiment of the flexible retainer for linking the segments of the implant;

FIG. 10 is a from plan view of a chin implant of the present invention illustrating the incorporation of a flexible retainer of the type illustrated in FIG. 9;

FIG. 11 is a front plan view of yet another alternate embodiment of the flexible retainer;

DETAILED DESCRIPTION OF THE INVENTION

The present invention comprises a prosthetic implant designed to repair, replace or augment the hard tissue or bone of a patient. For each specific body part to be treated, a standardized implant is provided which can be expeditiously shaped by the surgeon or practitioner to accommodate the contour of each individual.

This standardization and adaptability (flexibility) of the implants is achieved by forming the implant of two or more segments and linking the segments by a flexible member so that the individual segments can move in relation to one another. Such movement varies the overall shape and curvature of the implant to accommodate the body structure of the particular individual. Thus, rather than the surgeon molding or sculpting an implant to fit the patient as in the prior art, the surgeon can select the appropriate standardized implant and bend the segments to account for the structural variations, e.g. different contour, among patients.

Figure 1:
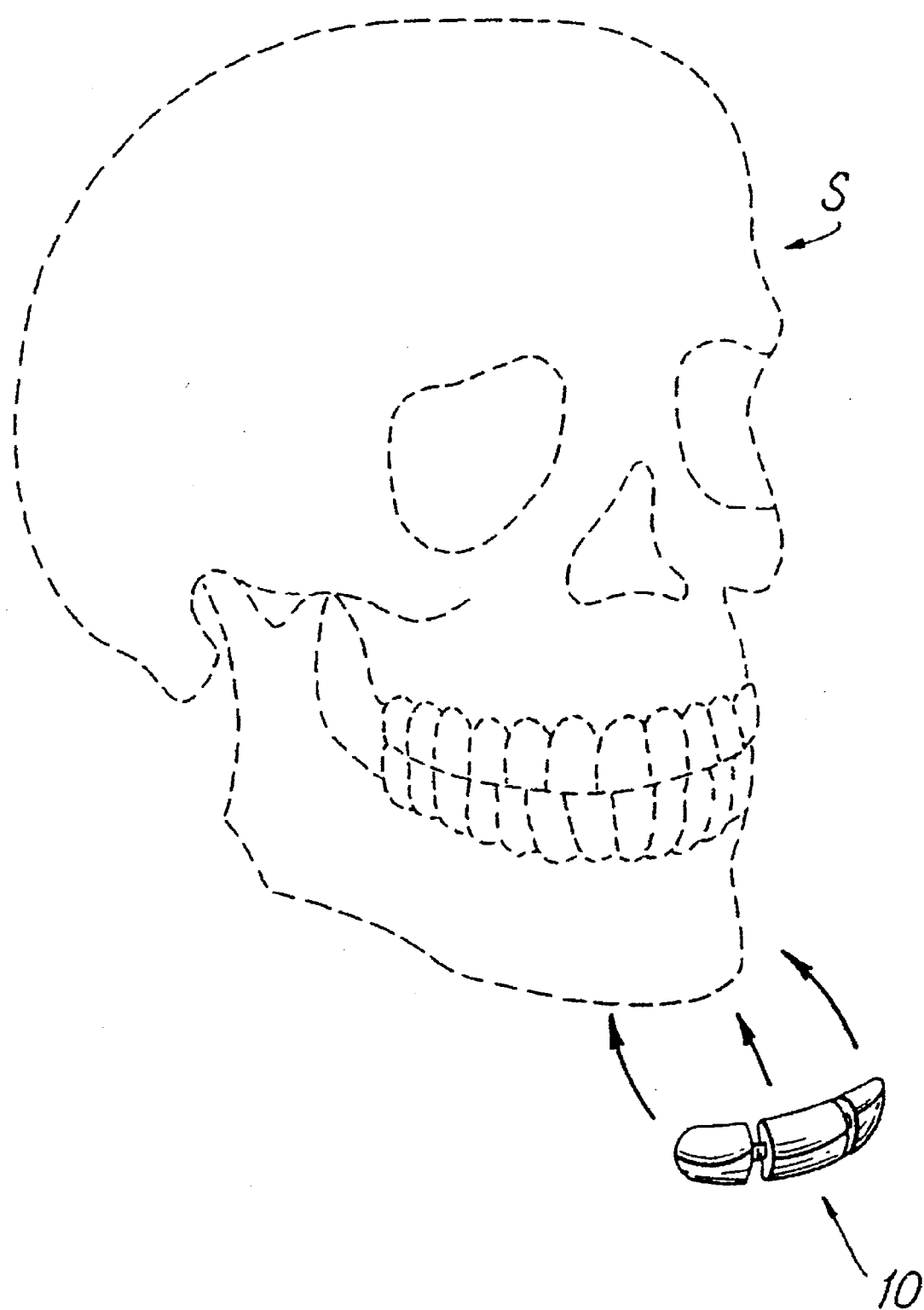
FIG. 1 is a front perspective view of a chin implant of the present invention showing the location of its placement on the human skull.
Figure 12A:
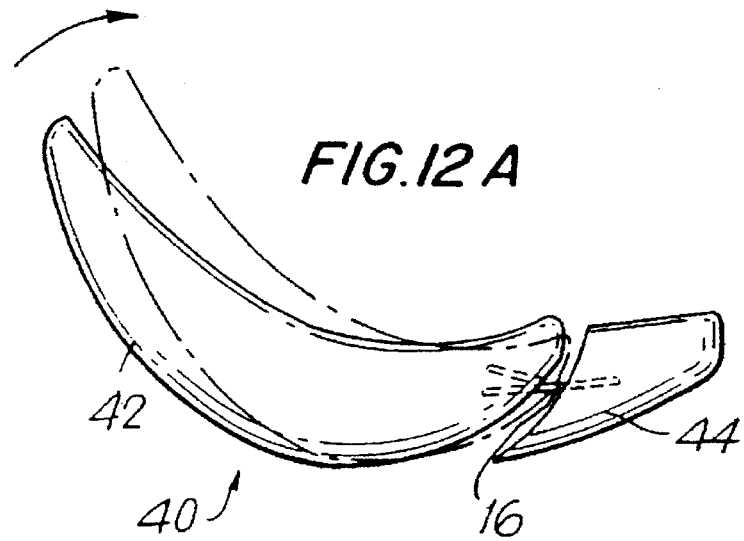
FIG. 12A is a top view of a fight side malar implant of the present invention showing in phantom the tail segment re-oriented.
Figure 12B:
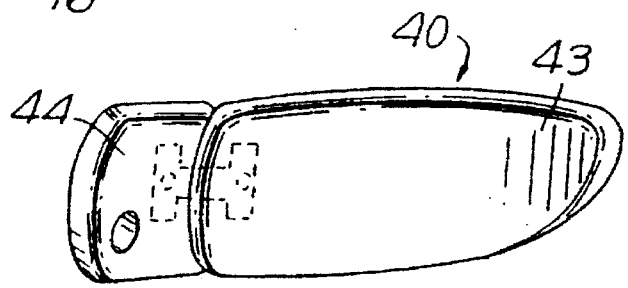
FIG. 12B is a rear view of the malar implant of FIG. 12A.
Figure 12C:
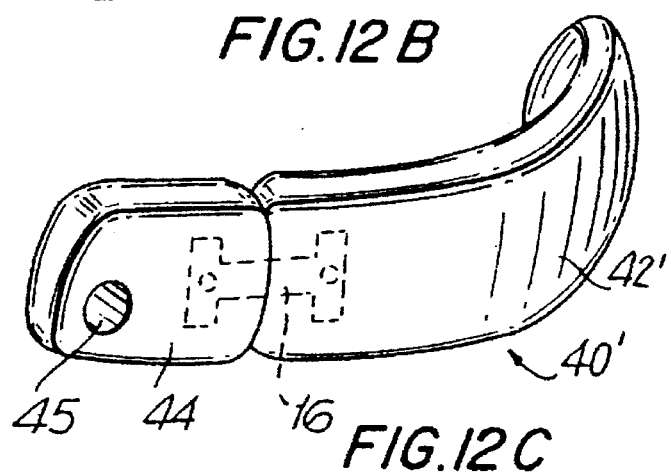
FIG. 12C is a front perspective view of a left side malar implant of the present invention.
Figure 14:
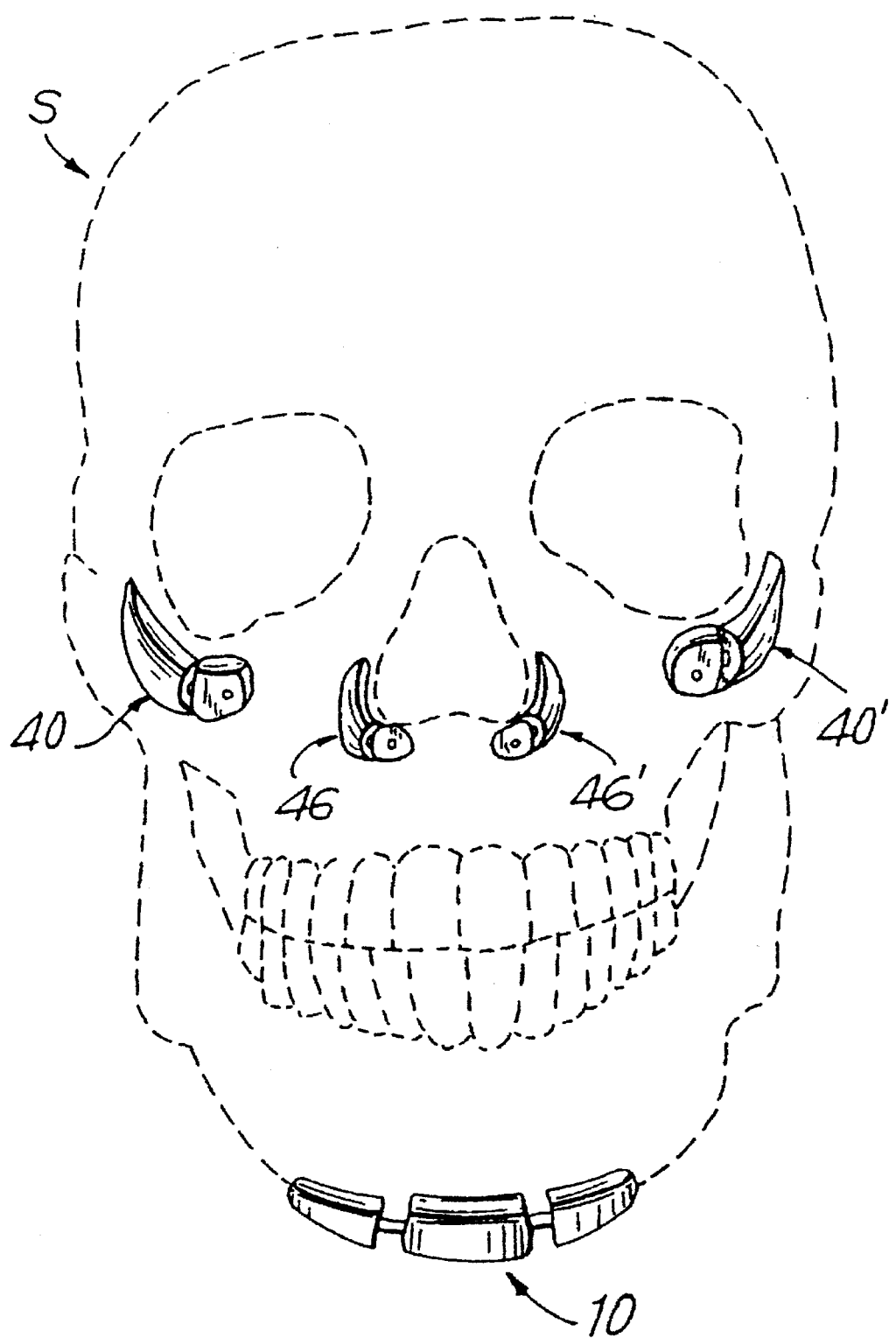
FIG. 14 is a front plan view of a human skull showing the anatomical positioning of the chin, malar and paranasal implants of the present invention.
Figure 15:
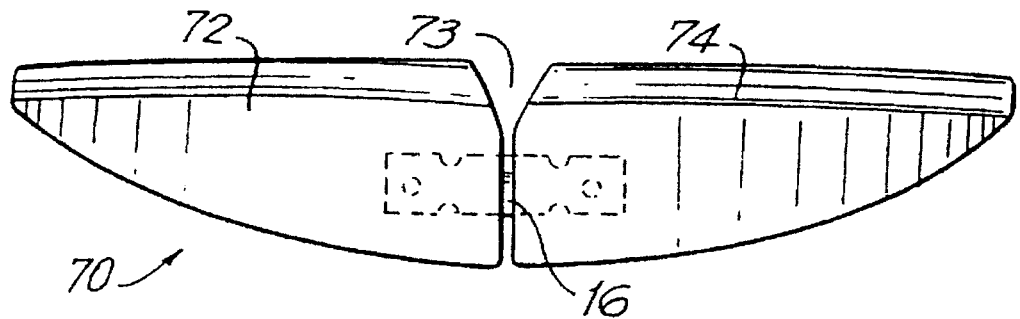
FIG. 15 is a front plan view of a premaxillary implant of the present invention.
Figure 16:
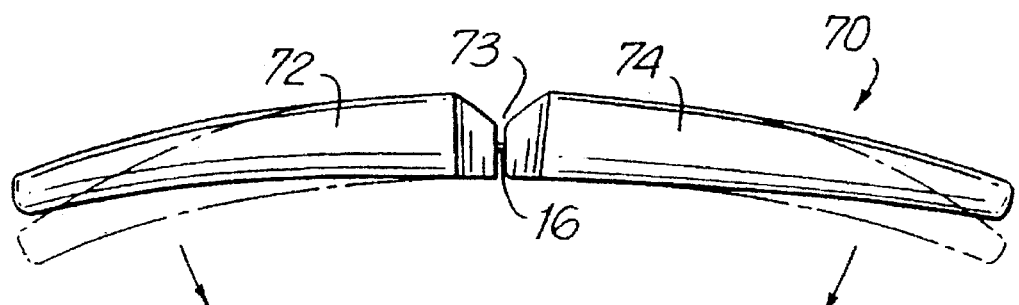
FIG. 16 is a top view of the premaxillary implant of FIG. 15.
Figure 17:
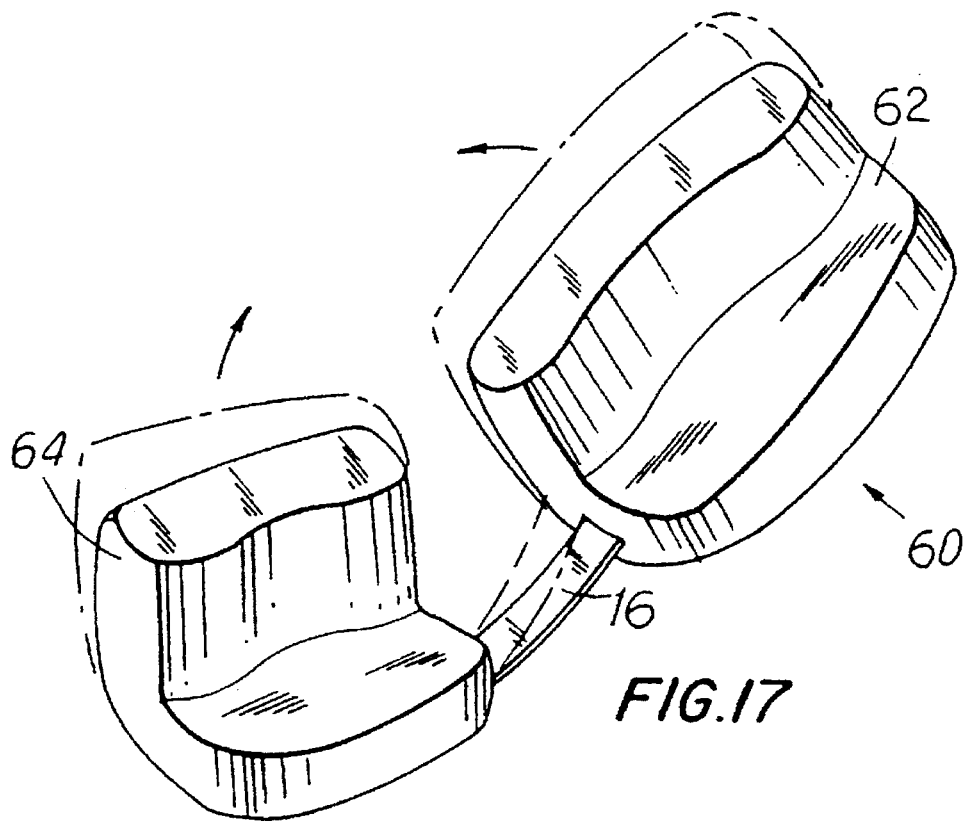
FIG. 17 is a rear perspective view of a left side gonial angle implant of the present invention.

The implants of the present invention designed to augment or repair maxillofacial body parts are shown in FIGS. 2A-2C, 12A-12C, 13A-13C and 15-17. A chin implant, designated by reference numeral 10 (FIGS. 2A-2C), is designed to be positioned to treat the lateral (external) anterior (front) portion of the mandible as shown in FIGS. 1 and 14 which illustrate the human skull S. A right and left side malar implant, designated by reference numerals 40 and 40', respectively, and shown in FIGS. 12A and 12C, are positioned to augment or replace the lateral portion of the right and left zygomatic bones, as illustrated in FIG. 14. A right and left side paranasal implant, designated in FIG. 13A-13C by reference numerals 46 and 46', respectively, are positioned to treat the lateral portion of the maxilla along the left and right sides of the inferior nasal concha. A left side gonial angle implant 60 is illustrated in FIG. 17 and a premaxillary implant 70 is illustrated in FIGS. 15 and 16.

As will become apparent from the discussion below, the present invention is not limited to chin, malar, paranasal, gonial angle or premaxillary implants, nor is it limited to maxillofacial implants; the present invention contemplates implants for any part of the body which require flexible parts to accommodate the body structure of the particular individual.

Figure 2A:
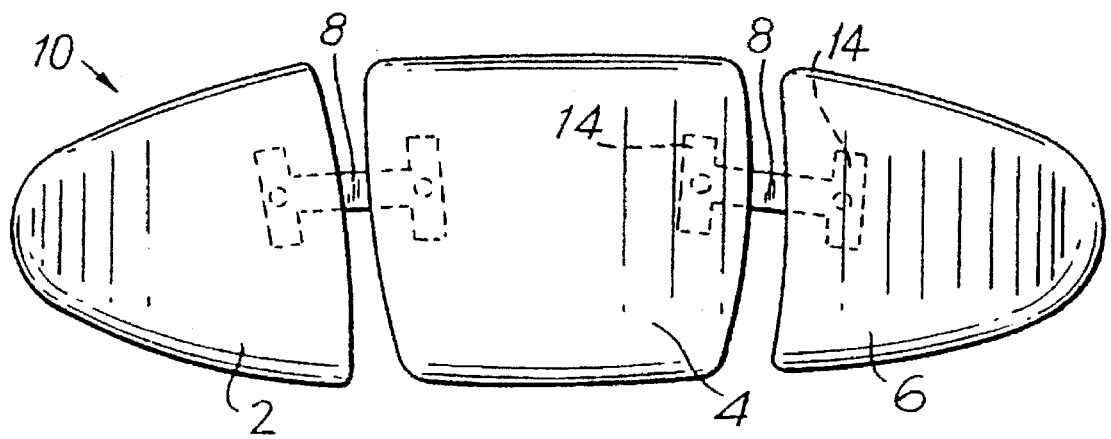
FIG. 2A is a front plan view of the implant of FIG. 1.
Figure 2B:
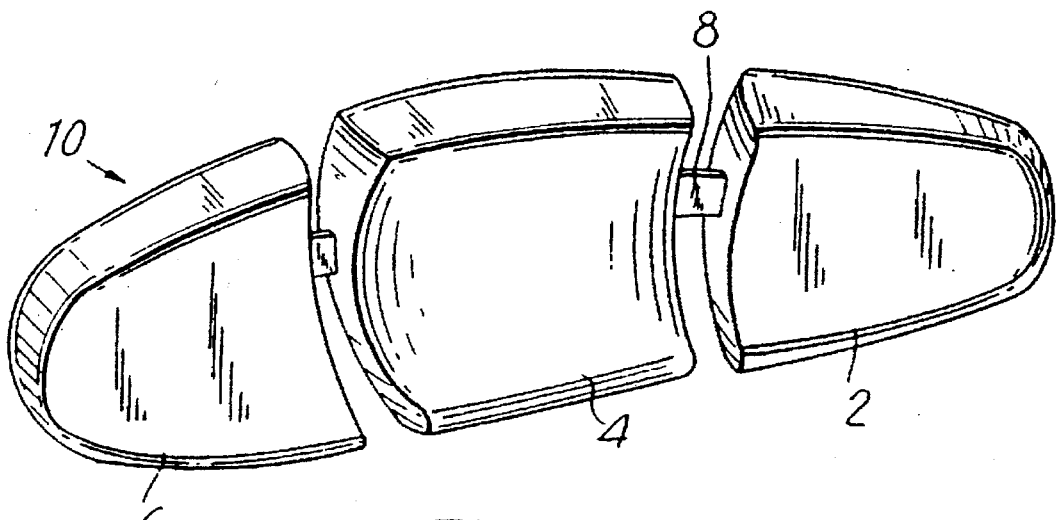
FIG. 2B is a rear view of the implant of FIG. 1.
Figure 2C:
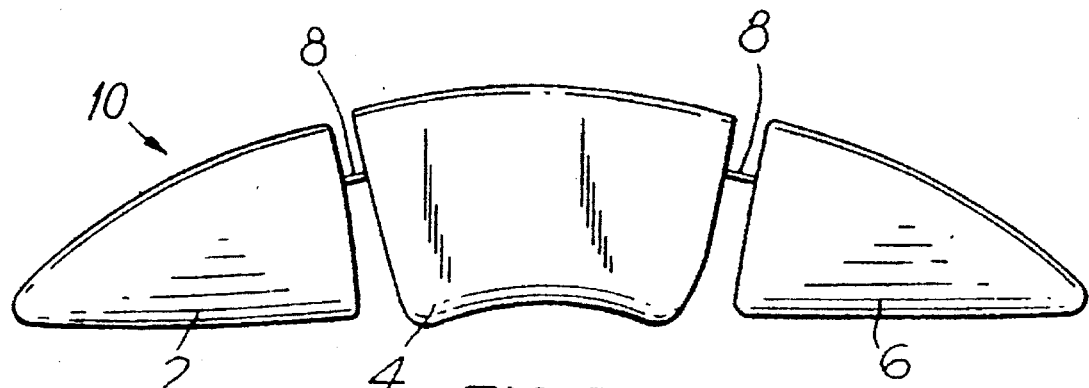
FIG. 2C is a bottom view of the implant of FIG. 1.
Figure 3:
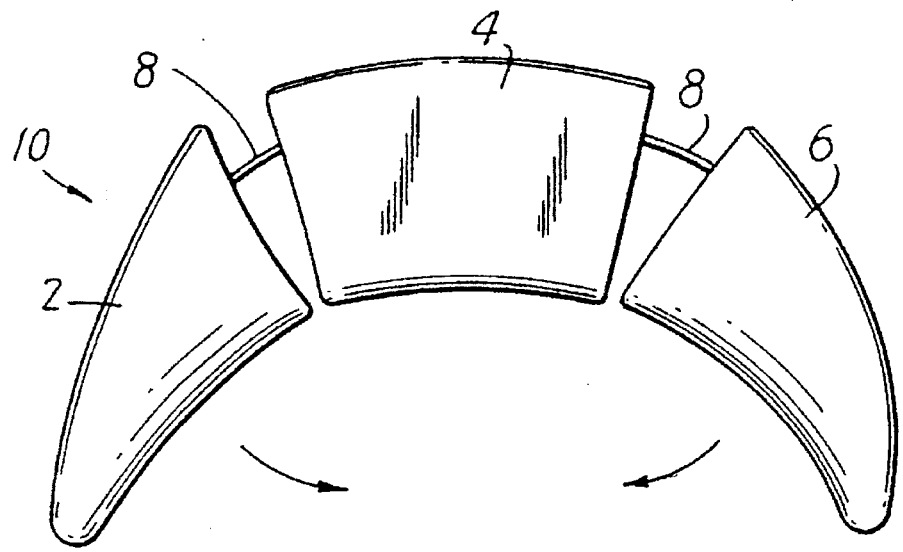
FIGS. 3 and 4 are bottom plan views of the implant of FIG. 2 with the segments re-oriented by being moved in the direction of the arrows.
Figure 4:
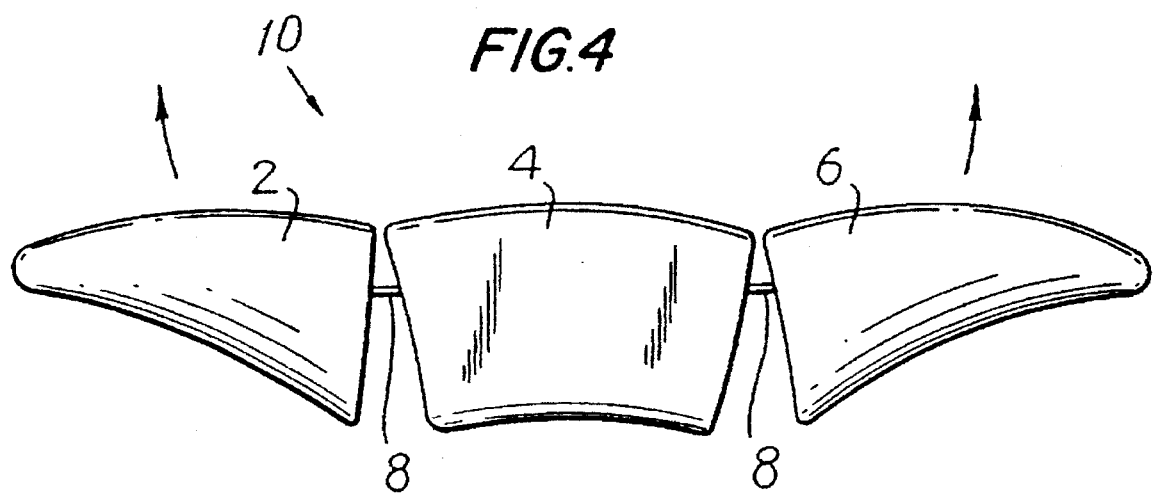

Turning first to the chin implant 10 and more particularly to FIGS. 2A-2C, chin implant 10 is composed of three segments: a first chin segment 2; a second or middle chin segment 4; and a third chin segment 6. The first and second segments 2 and 6 are each connected to the middle segment 4 by a retainer 8. As is more fully described below, the retainer 8 is made of a flexible material which allows segments 2 and 6 to be oriented at various angles in relation to segment 4 so the implant 10 can be adjusted to conform to a patient's bone structure. For example, to accommodate a chin having a smaller radius of curvature, segments 2 and 6 can be bent inwardly in the direction of the arrows to the configuration shown in FIG. 3. The retainers and implant can also be configured so that either or both segments 2 and 6 are not only capable of being moved inwardly (rearwardly), but can move forwardly (see FIG. 4 with the arrows depicting the direction of movement of the end segments), upwardly, downwardly, or in any other directions in relation to the other segments. The retainers for linking the segments which allow for their flexibility (adaptability) are described in detail below.

A malar implant fashioned for the lateral portion of the right and left zygomatic bone is illustrated in FIGS. 12A-12C. The right-side malar implant 40 (FIG. 12A) is composed of two segments: an upper segment 42 and a lower segment 44. A retainer 16 is shown by way of example to traverse the gap between segments 42 and 44 to link them together. The flexibility of upper segment 42 is indicated in phantom in FIG. 12A as it is bent inwardly in the direction of the arrow. The left-side flexible malar implant 40', illustrated in FIG. 12B, is essentially a mirror image of the right-side malar implant 40 and comprises upper segment 40' linked to lower segment 44' by retainer 16. As in chin implant 10, the malar implants 40, 40' can be configured and fashioned with a flexible member that allows bending of one or both segments in directions other than that illustrated in FIG. 12A. Screw hole 45 can be provided for attachment of the implants to the facial bones of the skull.

Figure 13A:
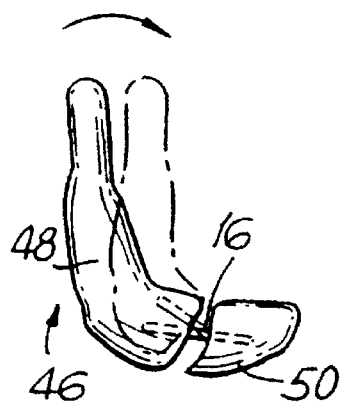
FIG. 13A is a top view of a fight side paranasal implant of the present invention showing in phantom the tail segment re-oriented.
Figure 13B:
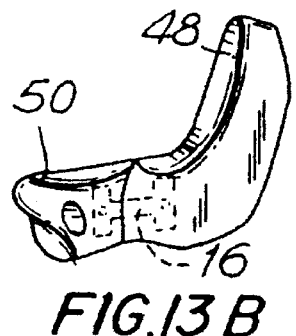
FIG. 13B is a rear view of the paranasal implant of FIG. 13A.
Figure 13C:
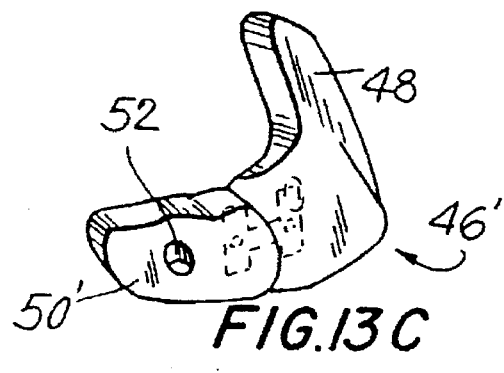
FIG. 13C is a front perspective view of the left side paranasal implant of the present invention.

FIGS. 13A-13C illustrate flexible paranasal implants of the present invention which are designed to augment the lateral portion of the maxilla along the left and right sides of the inferior nasal concha. The right-side paranasal implant 46 is composed of two segments: an upper segment 48 and a lower segment 50, linked together by a retainer 16. Implant 46 is shown in FIG. 13A with upper segment 48 bent inwardly in the direction of the arrow to the position shown in phantom to illustrate the flexibility of the implant. The left-side paranasal implant 46' shown in FIG. 13C is a mirror image of the right-side paranasal implant 46 and comprises an upper segment 48' linked to a lower segment 50' by a retainer 16 and is bendable in the same manner as right side paranasal implant 46'. As is apparent, similar to malar implants 40, 40', the retainer and the upper and lower segments of the paranasal implants can be configured to move in a virtually limitless number of directions with respect to one another to allow re-orientation to fit the needs of the particular patient. The paranasal implants 46, 46' may also have a screw-hole 52 for securement to the body.

A premaxillary implant 70, illustrated in FIGS. 15 and 16, is positioned at the base of the pyriform aperture behind the upper lip (see FIG. 18) to elevate the nostril base and augment the paranasal-maxillary region. The implant provides a forward positioning of the anterior nasal spine and columella. A notch 73 is provided in the midline to accommodate the anterior nasal spine. The premaxillary implant 70 is composed of two segments 72 and 74 which are joined by a flexible connecting member (illustratively flexible connecting member 16 of FIG. 7) to allow re-orientation of the segments as shown in phantom in FIG. 16 to fit the contours of the patient's anterior maxilla. Clearly the segments can be moved in directions other than the direction depicted in FIG. 16.

Figure 18:
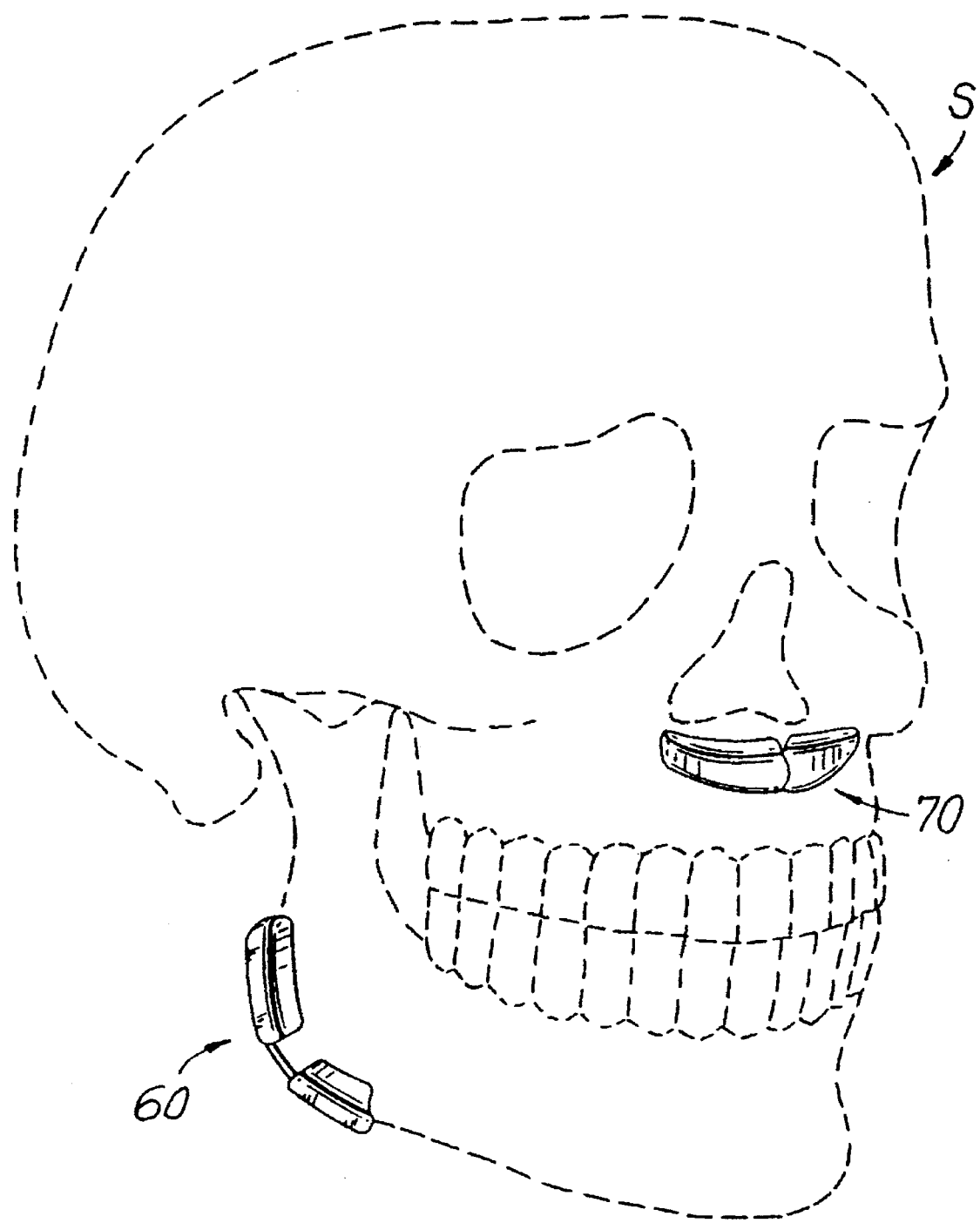
FIG. 18 is a front perspective view of a human skull showing the anatomical positioning of the premaxillary and left side gonial angle implants of the present invention.

FIG. 17 illustrates a left side gonial angle implant 60 fashioned for the gonial angle region of the mandible as shown in FIG. 18. The implant is composed of segments 62, 64 joined by a flexible connecting member 16 to allow re-orientation of the segments (shown in phantom) to fit the differing angular relationships between the inferior border and posterior ascending ramus of the mandible. The arrows indicate one of the numerous directions the segments can be moved to conform to the contour of the patient. The right side gonial implant (not shown) is the mirror image of the left side gonial angle implant 60.

The implants (i.e. segments) of the present invention are made of biologically compatible materials which are suitable for withstanding any reasonable stress to which they may be subjected after implantation. The segments should be strong and durable and, in certain cases, can be made to effectively induce the growth of tissue or bone in or around its location. In a preferred embodiment, a porous structure of a polymeric composite such as polymethylmethacrylate (PMMA) is coated with a polymeric hydrophilic material, such as polyhydroxyethylmethacrylate (PHEMA). Various materials which render the implant opaque to X-rays may also be incorporated, e.g., barium sulfate. These materials and processes for making these materials are disclosed in U.S. Pat. Nos. 4,547,390, 4,547,327, and 4,728,570, herein incorporated by reference. It is contemplated, however, that any other suitable prosthetic material which is known to those with skill in the art such as dense or porous ceramics, polymer/ceramic composites or metals can be used in accordance with the present invention. The materials can also include, for example, resorbable polymeric material such as copolymers of glycolide, lactide and/or polydioxanone.

The method of forming the segmented implants of the present invention with the retainers embedded therein will be discussed below. Note that in forming the segmented implants, the distance between adjacent segments may be varied to suit different applications. A greater distance between segments allows more of an angle to be achieved between adjacent segments. The distance between segments preferably ranges from 0.005 inches to 0.25 inches, however larger or smaller distances are within the scope of the present invention. In situations where the segments are spaced far apart, the void between segments may be filled with a bone substitute such as granular HTR® polymer, a trademark of United States Surgical Corporation. Moreover, a different number of segments then illustrated herein can be utilized (e.g. a larger number of segments for increasing flexibility) and the shape and configuration of the individual segments (e.g. the location of the segmentation) can vary depending on its use.

Although the chin implant 10, the paranasal implants 46 and 46', the malar implants 40 and 40', the gonial angle implant 60 and premaxillary implant 70 are illustrated as having longitudinal gaps between the segments, it is contemplated that the gaps can be latitudinal or diagonal as well. Indeed, latitudinal, longitudinal and diagonal gaps may be incorporated into the same flexible implant to allow segments to be positioned at all sorts of appropriate angles and directions. It is also contemplated that more than one flexible member can be used to traverse the gap at different points between segments (see e.g. FIG. 8B).

One with ordinary skill in the art may use any appropriate method or means that are known for attaching the implants of the present invention to the facial bones of the skull. For example, metal or plastics screws can be inserted through one or more of the segments of the implant material and secured to the body.

The segments of the implant of the present invention can be linked by any suitable retaining element which anchors the segments while allowing movement of the segments with respect to one another, and the retaining element can be made of a variety of materials. Optimum materials for the retainer are biocompatible, sufficiently flexible to allow movement of the segments, and sufficiently strong to be capable of holding the segments together, i.e., the segments should not be easily pulled apart. The materials should also be capable of withstanding the stress of bending without breaking. One preferred material is stainless steel (preferably 316 and 316L), of a thickness of about 0.005 inches to about 0.015 inches, which has sufficient strength to hold the segments together, while being sufficiently resilient to enable the implant to return to its original shape after being bent to the desired shape. Another preferred material is Commercially Pure grade Titanium (preferably Grade 1 to 4), of a thickness of about 0.005 inches to about 0.015 inches, which has the advantage of being strong as well as malleable so the implant can be bent to the desired shape and remain in that form. Other materials which can be utilized for the retainers include silicon rubber, polyurethanes, polyesters such as Dacron® (E.I. DuPont de Nemours & Company), nylons, polyethylene, collagen fibers, aluminum oxides, carbon fibers and/or composites, titanium alloys, Co—Cr alloy and Co—Cr—Mo alloy. Additionally, in certain applications the retainer material can be made of a resorbable material, such as polymers or copolymers of glycolide, lactide, p-dioxanone, and the like. Resorbability is a desired characteristic if the implant itself, e.g. the segments, are composed of resorbable material. The surface of the retainer may also be roughened such as by sanding or providing pimples or pits to improve its bonding to the segments as will be described below.

As is apparent, materials other than those listed above can be utilized provided they allow the retainers to perform the function described herein. It should be noted that the material utilized will affect the flexibility of the implant, e.g. a woven mesh allows more flexibility between segments than metal. Additionally, the type of material might impact the holding strength of the adjacent segments. Different materials will also have different degrees of bonding to the segments, depending of course on the material of the segments.

Figure 5:
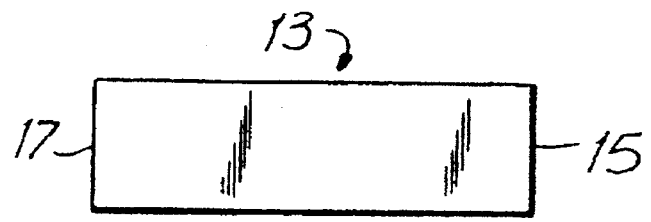
FIG. 5 is a front plan view of one embodiment of a flexible retainer of the present invention for linking the segments of the implant.

FIG. 5 illustrates one embodiment of a retainer for linking the segments. Retainer 13 is substantially rectangular in configuration and has opposing ends 15, 17 which are each secured to one of the adjacent segments. The retainer 13 can be set in the implant mold during formation of the implant as described below or fastened by other suitable means such as adhesive.

Figure 6:
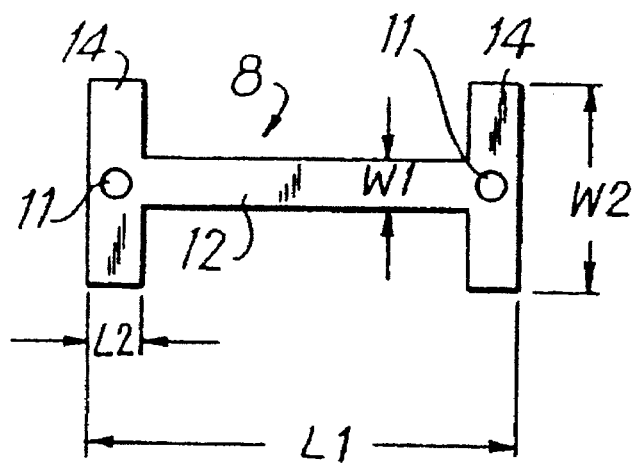
FIG. 6 is a front plan view of another alternate embodiment of a flexible retainer.

Another type of retainer which can be utilized to link the segments is illustrated in FIG. 6. The retainer 8 is I-shaped in configuration and is shown inserted between the chin segments 2 and 4 and between the chin segments 4 and 6 in FIG. 2A. Flanges 14 are provided to help achieve the desired snug and stable bond with the segments, to anchor the retainer 8 within the segments, and to restrict lateral movement of the segments. Cross member 12 is the locus of the bend when the implant is conformed to fit a patient's body structure. An anchor hole 11 can be provided to permit the pre-cured or molten segment material to flow through the hole 11 and surround the retainer 8 during formation of the implant. When the material hardens or cures around the hole 11, it helps stabilize the retainer in the cured or hardened segment.

Figure 7:
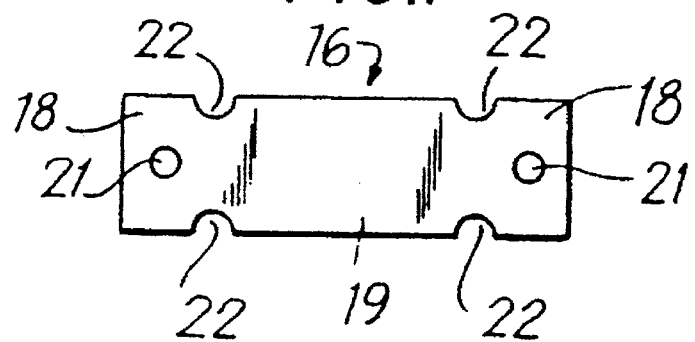
FIG. 7 is a front plan view of yet another alternate embodiment of the flexible retainer.
Figure 8A:
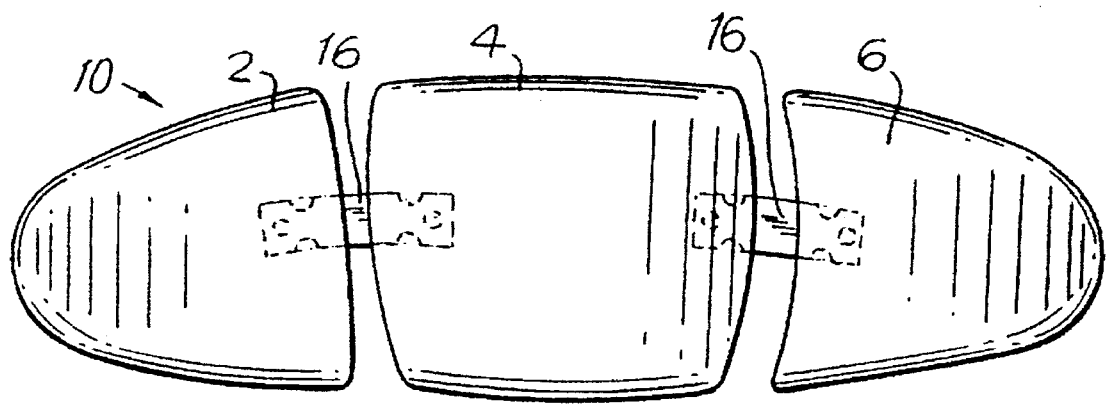
FIG. 8A is a front plan view of a chin implant of the present invention illustrating the incorporation of a flexible retainer of the type illustrated in FIG. 7.

Another alternate embodiment of the retainer is shown in FIG. 7 wherein the retainer, designated by reference numeral 16, has a discontinuous edge surface to provide an anchor 18 on both ends of the bending region 19. That is, notch 22 allows the pre-cured or molten segment material to flow around it and a flange 20 acts in a similar manner as the flanges 14 in FIG. 6. Additionally, an anchor hole 21, similar to anchor hole 11 of retainer 8 in FIG. 6, can be provided to permit the segment material to flow through to improve retention. The discontinuous retainer 16 is shown connecting chin segments 4 to segments 2 and 6 in FIG. 8A.

Another embodiment of the retainer which can be utilized to link the segments is illustrated in FIG. 9. Retainer 24 is made of woven material such as polyester, polyaramid, polyethylene, or polypropylene. A separate retainer may link middle segment 4 with segments 2 and 6, or alternatively, as shown in FIG. 10, a retainer 24' of sufficient length can be provided to extend from left end segment 6 through middle segment 4 to right end segment 2. A multiplicity of anchor holes 28 help to stably and snugly join the segments to the retainer 24 as they allow for material flow during formation of the implant. FIG. 11 shows an alternate embodiment in which the retainer 34 is made from meshwork 36 and anchor holes 35 achieve a similar result as holes 28 of the woven material. The mesh 36 can be composed of a woven or non-woven material. The retainer can alternately be composed of a material woven into a braid.

As is apparent, not only are different materials and configurations for the retainer contemplated, different sizes (e.g. thickness and length) can be utilized so long as they achieve the function of securing the adjacent segments and allow re-orienting the segments. For example, if a more rigid material such as titanium or steel is utilized, the retainer may be a flat shim or it can be round, such as a wire. The flat shape permits bending along the plane of the retainer while a circular or polygonal shape would permit a 360° range of bending. The length of the retainer can also vary. For example it can be of sufficient length to traverse the distance between two segments as shown, for example in FIG. 1, or it may be long enough to extend between all the segments as shown, for example in FIG. 6.

By way of example, in one embodiment, a stainless steel retainer of the type shown in FIG. 6 can be used which has a thickness of about 0.01 inches, a length L1 of approximately 0.40 inches, a width W1 of about 0.12 inches. The flanges 14 have a length L2 of about 0.070 inches and a width W2 of about 0.24 inches. Clearly, these dimensions are set forth by way of example only and the present invention is not limited to retainers of these dimensions.

Figure 8B:
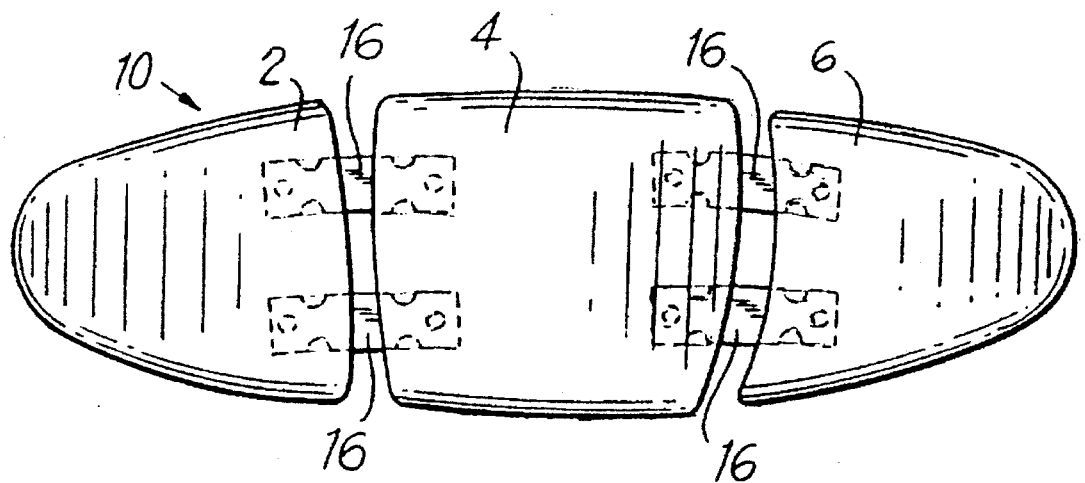
FIG. 8B is a front plan view of a chin implant of the present invention illustrating the incorporation of multiple flexible retainers of the type illustrated in FIG. 7.

Moreover, a multiplicity of either flat or round retaining elements can be provided, as shown for example in FIG. 8B, which would facilitate re-orientation e.g. rotational deformation, of the various segments.

Additionally, rather than provide a retainer of the types shown, a flexible material can be inserted to fill all or part of the gaps between adjacent segments to achieve the desired flexibility.

Turning now to formation of the implant of the present invention, the implant can be formed by making a model implant of a plastic material and dividing it into segments. A mold is made of the segments using a material such as silicon rubber and the segments are spaced apart the desired distance, preferably between about 0.005 and about 0.25 inches. The mold is partially filed with the desired implant material and a retainer is then placed in the mold so it bridges the gap between the segments and is embedded at each end in the segments. The mold is then completely filled with the implant material; the implant material covering the exposed surface of the retainer. The mold is closed (i.e. the posterior part of the mold is placed over the anterior part) and placed in a microwave oven to be cured, preferably for about 1 to 4 minutes. The method of making the implant of the present invention will be described in more detail with reference to the following example for forming a chin implant.

An SLA (stereolithography apparatus) model chin composed of a resin having an overall length of approximately 1.75 inches (although ranges from about 1–2½ inches are contemplated) and a width of approximately 0.2 inches (although ranges from about 0.1 to 0.3 inches are contemplated) was cut longitudinally into three segments in the inferior/superior (transverse) direction. A mold (anterior and posterior) using Citricon® silicon rubber, (Kerr Manufacturing Company), was made of the three cut segments such that each segment was placed within approximately ⅛ of an inch of the adjacent segment. After the mold was cured and emptied, it was composed of three cavities separated from each other by approximately ⅛ inch thick barrier walls. A longitudinal cut was made in the barrier walls that extended about halfway through the cross-section of the segment to allow insertion of an appropriate retainer.

The mold was partially filled with a molding resin comprising a blended mixture of about 300 grams of polymethymethacrylate (PMMA) beads introduced into a stirred mixture of about 45 grams of liquid hydroxyethymethacrylate (HEMA) and about 9 grams of barium sulfate. The average size of the beads was approximately 20/24 mesh (diameter ranging from about 710 to 851 microns). A retainer of stainless steel of the type shown in FIG. 6 was placed in the slots in the molded resin to bridge the barrier walls and extend into the segment. The mold was then closed, filled and cured in a microwave oven for about two minutes. The retainer securely held the segments together.

The present invention advantageously allows for standardization of implants since the segments can be oriented to accommodate the individual patient. For example, the particular implant e.g. chin, malar, or paranasal implant, can be made in a few sizes and then bent to conform to the facial contour of the patient in the size group. The present invention thereby provides a substantial time saving to the physician and cost saving to the patient by eliminating the need for preparing and using a custom mold or laboriously carving an implant to obtain the required configuration. If a prior art custom molded implant does not conform to the patient's body part, the practitioner will need to waste valuable time attempting to carve out the correct shape and may even need to fabricate an entirely new implant. If an error is made in bending an implant of the present invention, the practitioner just needs to either bend the implant to the correct shape or try a different size standard implant and then conform it to the patient's needs.

It should be noted that the examples and illustrations supplied herein are not to be construed as limitations of the inventive concept. Additionally, modifications and improvements may be made by those with skill in the art without departing from the spirit and scope of the invention.

What is claimed is:

1. A method of making a prosthetic implant comprising the steps of:

partially filling a mold having two spaced apart cavities with material suitable for forming prosthetic implants;

placing a flexible retainer between the two partially filled cavities so the retainer extends partially into each cavity;

filling said mold to cover the retainer;

curing the material to form a prosthetic implant; and removing the prosthetic implant from the mold wherein the prosthetic implant includes at least two segments which are connected by the flexible retainer such that the segments and the flexible retainer cooperate to conform the prosthetic implant to the contour of at least a portion of underlying maxillofacial bone.

2. A method of making a prosthetic implant comprising:

a) placing at least two segments in an adjacently spaced apart relation;

b) molding around said segments so as to form a mold having at least two cavities which are separated from one another by at least one wall of said mold;

c) removing a portion of said at least one wall, the portion corresponding to the size and shape of a retaining member to permit the retaining member to be situated to traverse adjacent cavities;

d) partially filling said mold cavities with a material suitable for forming prosthetic implants;

e) placing a flexible retainer member between said adjacent cavities such that said retainer member traverses said wall between adjacent cavities;

f) further filling said mold cavities with the material suitable for forming prosthetic implants;

g) curing the material suitable for forming prosthetic implants so as to form a prosthetic implant having at least two segments connected by the flexible retaining member; and h) removing the prosthetic implant from the mold wherein the segments and the flexible retaining member cooperate to conform the prosthetic implant to at least a portion of underlying maxillofacial bone.

3. A method according to claim 2, wherein said material for forming the prosthetic implant is composed of polymethylmethacrylate polyhydroxyethylmethacrylate composite.

4. A method of making a prosthetic implant comprising:

providing a mold having two spaced apart cavities;

placing a flexible retainer between the two spaced apart cavities so the retainer extends partially into each cavity;

filling the mold with material suitable for forming prosthetic implants;

curing the material to form a prosthetic implant; and removing the prosthetic implant from the mold wherein the prosthetic implant includes at least two segments which are connected by the flexible retainer such that the segments and the flexible retainer cooperate to conform the prosthetic implant to the contour of at least a portion of underlying maxillofacial bone.

* * * * *